United States Patent
Ku et al.

(10) Patent No.: US 9,897,920 B2
(45) Date of Patent: Feb. 20, 2018

(54) SENSOR FOR DETECTING SACCHARIDE AND MANUFACTURING METHOD THEREOF AND DETECTION METHOD OF GLYCATED HEMOGLOBIN USING THE SAME

(71) Applicants: LG ELECTRONICS INC., Seoul (KR); AJOU UNIVERSITY INDUSTRY-ACADEMIC COOPERATION FOUNDATION, Suwon-si, Gyeonggi-do (KR)

(72) Inventors: Yunhee Ku, Seoul (KR); Moosub Kim, Seoul (KR); Yongju Yang, Seoul (KR); Seung Yeon Song, Seoul (KR); Kang Sun Lee, Seoul (KR); Hyun Chul Yoon, Seoul (KR); Yong Duk Han, Seongnam-si (KR); Yoo Min Park, Seoul (KR)

(73) Assignees: LG ELECTRONICS INC., Seoul (KR); AJOU UNIVERSITY INDUSTRY—ACADEMIC COOPERATION FOUNDATION, Suwon-si (KR)

( * ) Notice: Subject to any disclaimer, the term of this patent is extended or adjusted under 35 U.S.C. 154(b) by 195 days.

(21) Appl. No.: 14/645,009

(22) Filed: Mar. 11, 2015

(65) Prior Publication Data

US 2016/0109370 A1 Apr. 21, 2016

(30) Foreign Application Priority Data

Oct. 21, 2014 (KR) .................. 10-2014-0142388

(51) Int. Cl.

| | | |
|---|---|---|
| *C12Q 1/54* | (2006.01) | |
| *C12Q 1/28* | (2006.01) | |
| *C12Q 1/00* | (2006.01) | |
| *G03F 7/20* | (2006.01) | |
| *G01N 21/78* | (2006.01) | |
| *G03F 7/027* | (2006.01) | |

(52) U.S. Cl.
CPC ........... *G03F 7/2002* (2013.01); *G01N 21/78* (2013.01); *G03F 7/027* (2013.01); *G01N 2400/00* (2013.01)

(58) Field of Classification Search
None
See application file for complete search history.

(56) References Cited

U.S. PATENT DOCUMENTS

| | | | | |
|---|---|---|---|---|
| 6,475,750 | B1 * | 11/2002 | Han ................... | A61B 5/14532 435/14 |
| 7,473,551 | B2 * | 1/2009 | Warthoe ................ | B82Y 15/00 310/311 |
| 2006/0076237 | A1 * | 4/2006 | Pluskal ................. | B01D 57/02 204/450 |
| 2009/0191642 | A1 * | 7/2009 | Wang ..................... | G01N 33/66 436/95 |
| 2012/0150006 | A1 * | 6/2012 | Lavanant ............... | C12Q 1/006 600/347 |

FOREIGN PATENT DOCUMENTS

WO   WO 00/10007   *   2/2000   ........... G01N 33/487

OTHER PUBLICATIONS

Alexeev et al., Anal. Chem., 75:2316-2323 (2003).*
Guan et al., Chem. Soc. Rev., 42:8106-8121 (2013).*
Lacina et al., Chem. Cent. J., 8(60)1-17 (2014).*
Ma et al., J. Electroanal. Chem., 580:348-352 (2005).*
Park et al., 18th Internat., Conf. Mini. Sys. Chem. Life Sci., pp. 1981-1983, Oct. 26-30, 2014.*
Sajid et al (J. Saudi Chem.Soc., 19:689-705 (2015).*
Wu et al, Chem. Soc. Rev., 42:8032-8048 (2013).*

* cited by examiner

*Primary Examiner* — Thomas J Visone
(74) *Attorney, Agent, or Firm* — Lee, Hong, Degerman, Kang & Waimey (57) ABSTRACT

The present disclosure relates to a sensor for detecting saccharide and manufacturing method thereof and detection method of glycated hemoglobin using the same wherein the sensor for detecting saccharide includes a reactive layer synthesized with hydrogel having a boronic acid-modified 3D mesh structure. A selective and sensitive detection of the glycated protein including glucose or glycated hemoglobin ($HbA_{1c}$) in blood through high level of signal may be enabled, and the durability of the sensor for detecting saccharide may be enhanced.

11 Claims, 7 Drawing Sheets

FIG. 1

(in DMSO)

SENSOR FOR DETECTING SACCHARIDE AND MANUFACTURING METHOD THEREOF AND DETECTION METHOD OF GLYCATED HEMOGLOBIN USING THE SAME

Pursuant to 35 U.S.C.§ 119 (a), this application claims the benefit of earlier filing date and right of priority to Korean Patent Application No. 10-2014-0142388, filed on Oct. 21, 2014, the contents of which are hereby incorporated by reference in their entirety.

TECHNICAL FIELD

The present disclosure relates to a sensor for detecting saccharide, and in particular to a sensor for detecting saccharide and manufacturing method thereof and detection method of glycated hemoglobin using the same wherein the sensor for detecting saccharide includes a reactive layer synthesized with hydrogel having a boronic acid-modified 3D mesh structure.

BACKGROUND ART

By increase of the population of obese people and life expectancy caused by fast growing industrialization, the diabetes mellitus (DM) is easy to find in the people of all ages, and the number of such people continues to increase.

What is most frequently used as a key index reflecting the level of blood glucose in the diabetes mellitus (DM) is blood glucose and glycated hemoglobin ($HbA_{1c}$). Since the glycated hemoglobin is known to cause less errors in examination conducted based on empty stomach and taking medicine. With the aid of the glycated hemoglobin, it is possible to estimate a long term development of the previous level of blood glucose before the moment blood was collected from a diabetic patient, for thereby usefully controlling and evaluating blood plasma for a long time period. Since the specificity is good, the glycated hemoglobin may be a good index for estimating diabetes and its complication. In consideration that the lifespan of red blood cell is 120 days, the glycated hemoglobin well reflects the average state of blood glucose for the recent 1~3 months, more particularly, the glycated hemoglobin intensively reflects a change in the blood glucose for one month period.

In addition to the blood glucose, the glycated hemoglobin is regarded as an important index for judging the diagnosis and treatment of diabetes through the examination of glycated hemoglobin. In the year of 2010, the American Diabetes Association (ADA) more actively updates the diagnosis standards which recommend performing the glycated hemoglobin examination during the diagnosis of diabetes.

The fixed criteria of the glycated hemoglobin may be expressed in a form of the percentage (%) of fraction of the glycated hemoglobin with respect to the total quantity of hemoglobin. In case of a normal person who is not a diabetic patient, they have glycated hemoglobin of below 5~6%. In case of a diabetic patient, the ratio of the glycated hemoglobin in blood is in excessive of 7%, and in case of a person who has a glycated hemoglobin ratio of around 7%, a more aggressive control and measurement with respect to the level of blood glucose is necessary through an additional management. Therefore, the detected concentration which has the most important meaning in terms of the measurement of glycated hemoglobin is a 7% section of glycated hemoglobin. For this reason, the development of a glycated hemoglobin measuring system which is capable of precisely differentiating the levels between 6.9% and 7% based on the above 7% section is required.

The development and application of the reactive layer which has a high selectivity and reactive efficiency with respect to the detection target substances are important so as to precisely and sensitively detect the target substances. Here, the reactive layer should selectively react with respect to a small quantity of detection target substance, and a high level of reaction yield should be guaranteed. For this, a recognition substance reacting with the detection target substance should exist in the reactive layer with a high concentration.

Generally, for immobilization of the target recognition substance with respect to a bio-sensing substrate, methods such as a simple adsorption method, a static electricity-based binding method, a self-assembled monolayer (SAM), etc. have been used. Especially, with the SAM technology, a well arranged 2D biological substance may be fixed on the surface of a solid substrate. The SAM technology is widely used in manufacturing an electrochemical and optic biosensor, since the SAM technology provides a relatively easier surface modification and biological substance treatment process as compared with other technologies.

However, the detection target substance can bind only with a monolayer structure over a limited 2D plane area on the reactive layer to which the SAM technology is applied. Thus, this may cause a spatial limitation to the binding reaction with more detection target substances. Also, it is disadvantageous that the SAM technology may be applied only to the limited materials such as a gold- or chemical-processed silicon substrate.

To resolve the above problems, a big attention is paid on developing and introducing a new structured reactive layer having a 3D structure rather than a 2D structure, wherein a target recognition substance is integrated with a high density in a corresponding structure to more efficiently and sensitively recognize a detection target substance. In addition, the development of a reactive layer which may be applied to a substrate made from a more economical material like a paper or a membrane, not a substrate which has a high manufacturing cost like the typical metallic electrode, etc. is required.

As for the glycated hemoglobin biosensor, it is reported that a boronic acid (BA), which can binds with a saccharide substance via cis-diol bond, is used as a recognition substance for glycated hemoglobin, and a boronic acid SAM may be formed at the surface of a gold electrode using a substance like a mercaptophenyl boronic acid. However, such methods may have limits in the glycated hemoglobin binding yield due to the 2D space limitation, and in that they are only applicable on the metal surface.

Therefore, in order to implement more sensitive glycated hemoglobin detection, the development of a new structured reactive layer wherein a boronic acid is arranged with a high density in a 3D structure in the limited area is required.

SUMMARY OF THE DISCLOSURE

Accordingly, the present disclosure is made in an effort to resolve the above-described problems. An object of the present disclosure is to provide a sensor for detecting saccharide, including a reactive layer which is synthesized with hydrogel having a boronic acid-modified 3D mesh structure.

To achieve the above objects, in a general aspect of the present disclosure, there is provided a sensor for detecting saccharide, comprising: a reactive layer synthesized with a boronic acid-modified hydrogel; and a porous membrane substrate fixed with the reactive layer.

In some exemplary embodiments of the present disclosure, the saccharide may be a saccharide portion of glycated protein or glucose.

In some exemplary embodiments of the present disclosure, the glycated protein may be glycated hemoglobin ($HbA_{1c}$).

In some exemplary embodiments of the present disclosure, the hydrogel may be photo-polymerized including a polymer monomer, a polymer cross-linker and the boronic acid in the porous membrane substrate.

In some exemplary embodiments of the present disclosure, the polymer monomer may be an acrylamide derivative, the polymer cross-linker may be an acrylamide derivative having two N functional groups (N,N'-), and the boronic acid may be a boronic acid having acryl groups.

In some exemplary embodiments of the present disclosure, the polymer monomer may be N-(2-hydroxyethyl)acrylamide, and the polymer cross-linker may be N,N'-methylene-bisacrylamide.

In some exemplary embodiments of the present disclosure, the boronic acid may be 3-(acrylamido)phenylboronic acid.

In some exemplary embodiments of the present disclosure, that the porous membrane substrate may be a substrate using a membrane for a LFA (Lateral Flow Assay) formed of glass fibers.

In addition, in another general aspect of the present disclosure, there is provided a method for manufacturing the sensor for detecting saccharide, comprising: injecting a polymer monomer, polymer cross-linker, the boronic acid, and a photo-polymerization reaction initiator into the porous membrane substrate; patterning the porous membrane substrate with a photo mask; irradiating UV (ultraviolet) onto the patterned porous membrane substrate; washing the UV-irradiated porous membrane substrate; and drying the washed porous membrane substrate.

In some exemplary embodiments of the present disclosure, the polymer monomer may be an acrylamide derivative, the polymer cross-linker may be an acrylamide derivate having two N functional groups (N,N'-), and the boronic acid may be a boronic acid having acryl groups.

In some exemplary embodiments of the present disclosure, the polymer monomer may be N-(2-hydroxyethyl)acrylamide, and the polymer cross-linker may be N,N'-methylene-bisacrylamide, and the boronic acid may be 3-(acrylamido)phenylboronic acid, and the N-(2-hydroxyethyl)acrylamide, the N,N'-methylene-bisacrylamide, the 3-(acrylamido)phenylboronic acid and the photo-polymerization reaction initiator may be mixed in a dimethyl sulfoxide solvent, and with respect to the dimethyl sulfoxide solvent, the weight ratio of N-(2-hydroxyethyl)acrylamide may be 8.00~10.00% (w/v), the weight ratio of N,N'-methylene-bisacrylamide may be 0.40~0.50% (w/v), the weight ratio of 3-(acrylamido)phenylboronic acid may be 0.10~2.00% (w/v), and the weight ratio of the photo-polymerization reaction initiator may be 0.05~0.14% (w/v).

In some exemplary embodiments of the present disclosure, the porous membrane substrate may be a substrate using a membrane for a LFA (Lateral Flow Assay) formed of glass fibers.

In addition, in still another general aspect of the present disclosure, there is provided a method for detecting glycated hemoglobin, comprising: mixing glycated hemoglobin and horseradish peroxidase on the sensor for detecting saccharide and reacting the mixed glycated hemoglobin and the horseradish peroxidase; washing a non-reactive protein after the reaction; inducing a color development by dripping a chromogen working solution including a chromogen and a substrate with respect to the horseradish peroxidase onto the sensor for detecting saccharide; and digitizing the degree of the color development and outputting the digitized degree.

In some exemplary embodiments of the present disclosure, the substrate is hydrogen peroxide, and the chromogen may be any one selected from the group consisting of 3,3',5,5'-tetramethylbenzidine, o-phenylenediamine dihydrochloride, 2,2'-azinobis[3-ethylbenzothiazoline-6-sulfonic acid]-diammonium salt, 3,3'-diaminobenzidine tetrahydrochloride, SAT-3 (analog of o-tolidine), N-ethyl-N-(2-hydroxy-3-sulfopropyl)-3-methoxyaniline sodium salt dihydrate, N-ethyl-N-(3-sulfopropyl)-3-methoxyaniline sodium salt monohydrate, N-ethyl-N-(3-sulfopropyl)aniline, sodium salt, N-ethyl-N-(2-hydroxy-3-sulfopropyl)-3,5-dimethoxyaniline sodium salt, N-(2-hydroxy-3-sulfopropyl)-3,5-dimethoxyaniline sodium salt), N,N-Bis(4-sulfobutyl)-3,5-dimethylaniline disodium salt, N-ethyl-N-(2-hydroxy-3-sulfopropyl)-3,5-dimethylaniline sodium salt monohydrate, N,N-Bis(4-sulfobutyl)-3-methylaniline disodium salt, N-ethyl-N-(2-hydroxy-3-sulfopropyl)-3-methylaniline sodium salt dihydrate and N-ethyl-N-(3-sulfopropyl)-3-methylaniline sodium salt monohydrate.

In some exemplary embodiments of the present disclosure, the mixing glycated hemoglobin and the horseradish peroxidase and the reacting the mixed glycated hemoglobin and the horseradish peroxidase on the sensor for detecting saccharide may be dropping a solution prepared by mixing the horseradish peroxidase and glycated hemoglobin resolved with the concentration of 1 to 10 μg/ml at a volumetric ratio of 1:1 in a PBS solution onto the sensor for detecting saccharide in an amount of 1 to 100 μl and reacting the mixed solution for 10 to 600 seconds.

Accordingly, the present disclosure has effects of enabling selective and sensitive detection of glycated protein including glucose or glycated hemoglobin ($HbA_{1c}$) in blood through a high signal level and enhancing the durability of a sensor for detecting saccharide.

DETAILED DESCRIPTION OF THE DISCLOSURE

The present disclosure may be modified in various forms and may have a variety of embodiments. The specific exemplary embodiments will be described throughout the description of the present disclosure.

Such a description is not intended to limit to a specific embodiment type and should be interpreted to include all modifications, equivalents and alternatives which are included in the concept and technical scope of the present disclosure.

Furthermore, the terms in the present application are used so as to describe the specific exemplary embodiment, not limiting the present disclosure. Unless otherwise defined in this description, all the terms used including the technical or scientific terms should be interpreted to have the same meaning as those which are generally understood by a person having ordinary skill in the art.

The exemplary embodiments of the present disclosure will be described below.

The present disclosure is directed to a sensor for detecting saccharide, which includes a reactive layer synthesized with a boronic acid-modified hydrogel, and a porous membrane substrate fixed by the reactive layer.

The boronic acid becomes a bioreceptor which is specifically and covalently bonded with a cis-diol group of saccharide for thereby specifically recognizing saccharide. Therefore, the boronic acid may recognize a saccharide having cis-diol groups or a glycated protein which is glycosylated by the saccharide having cis-diol groups. For example, the boronic acid may recognize the glucose from monosaccharides by the cis-diolbond. Since the boronic acid may recognize a portion of saccharide of the glycated protein of which the protein is glycosylated as well as a free sugar itself, it may become a receptor which may detect even the glycated protein. More specifically speaking, the boronic acid may become a bioreceptor with respect to the biological substance including saccharide.

Figure 2:
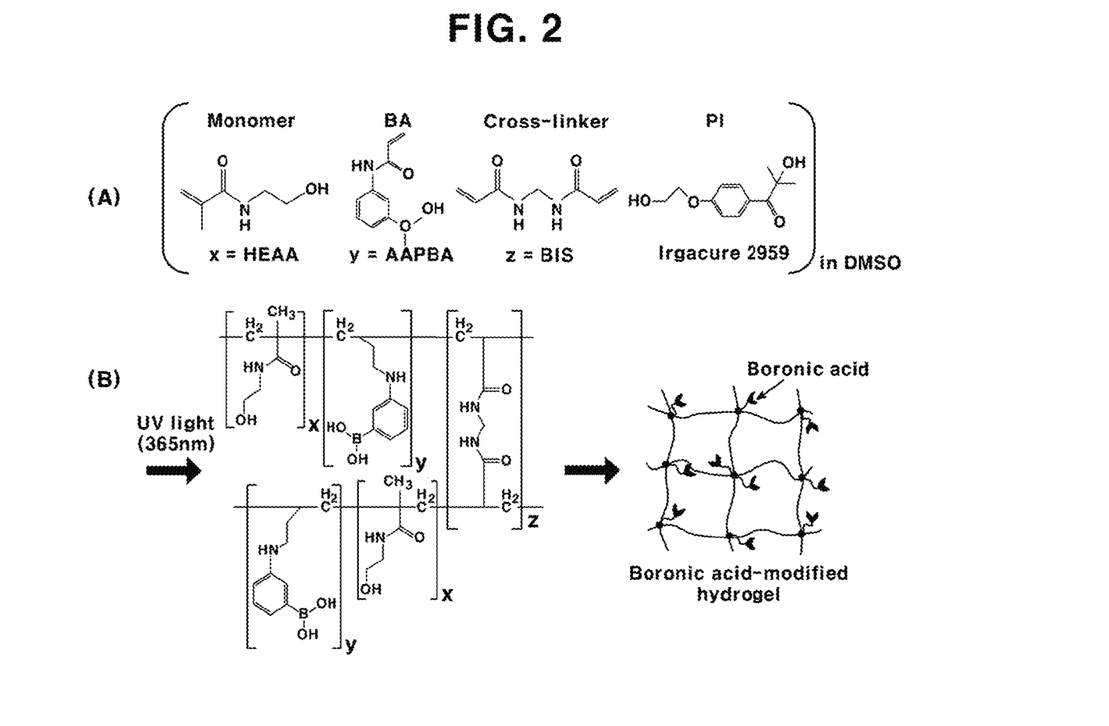
FIG. 2 is a mimetic diagram illustrating a procedure where hydrogel is synthesized using HEAA, BIS and AAPBA according to an exemplary embodiment of the present disclosure.

The hydrogel is synthesized into a 3D mesh structure through a photo-polymerization reaction with boronic acid and becomes a bioreceptor layer, that is, a reactive layer. The reactive layer is obtained in such a way that boronic acid is integrated with a high density into the hydrogel through a photo-polymerization. As illustrated in FIG. 2, the photo-polymerization reaction is activated by the irradiation of ultraviolet ray, and hydrogel is formed when a polymerization reaction occurs in series since a polymer monomer, a polymer cross-linker and a boronic acid absorb light and become activated. At this time, the boronic acid is combined with the hydrogel while maintaining a cis-diol group which is a reactive group for the interaction with saccharide. More specifically, the hydrogel of the present disclosure does not lose a specific binding force with respect to a sugar chain which is a natural characteristic of the boronic acid. Furthermore, the reactive layer synthesized with the boronic acid-modified hydrogen forms a 3D mesh structure for thereby enhancing a binding integration level of boronic acid functional groups in the polymer.

The hydrogel may be synthesized based on the size of the free sugar with which the boronic acid reacts or may be synthesized based on the size of the glycated protein with which the boronic acid reacts, so the hydrogel may be synthesized with the optimum density and structure based on the object which will be detected. Therefore, the sensor for detecting saccharide according to the present disclosure may be used a marker of disease based on a variety of the glycated proteins including sugar chains.

For example, the concentration (w/v) of the polymer monomer: boronic acid for the synthesis into the reactive layer for the sake of the 3D mesh structure optimized for the use of the detection of the glycated hemoglobin in the glycated protein may be adjusted within a range of 4:1 to 100:1.

The sensor for detecting saccharide according to an exemplary embodiment of the present disclosure may be manufactured in such a way that in a state where hydrogel precursor including a polymer monomer, a polymer cross-linker and a boronic acid is invaded in the porous membrane substrate, the hydrogel is synthesized through a photo-polymerization by the irradiation of ultraviolet ray, and upon the synthesis, it is fixed at the porous membrane substrate, and the manufacture is finished. More specifically, since the photo-polymerization is performed in the porous membrane substrate, the type or size of the hydrogel may be manipulated depending on the characteristic of the substrate such as the thickness, moisture absorption amount or moisture absorption ratio of the porous membrane substrate. Since the reactive layer has a fixed type exterior of the porous membrane substrate, it becomes easier to handle and move as compared with when there is only the jelly type hydrogel. In addition, since it has a hydrogel form inside of the porous structure, the externally exposed area increases, so that the efficiency of the biological substance reaction may be enhanced. Furthermore, since the capillarity of the porous membrane substrate makes easier the movement of the washing liquid, it needs to perform the washing procedure which is necessary to the saccharide detection reaction in very simple and efficient ways.

In the exemplary embodiment of the present disclosure, the hydrogel may be photo-polymerized using a polymer monomer, a polymer cross-linker and a polymerization reaction initiator in the porous membrane substrate.

The polymer monomer represents the unit which becomes the material of the polymerization reaction. For example, an acrylamide derivative may be used.

The polymer cross-linker represents a reactive unimolecule which is used to strength the binding of the polymerization reaction and manipulate the durability reliability and cohesion of the photo-polymerized reactive layer by adding a cross-linking functional group. As the polymer cross-linker, an acrylamide derivative having two N-functional groups (N,N'-) may be used, but it is not limited thereto. In addition to the monomer having a N-functional group, a monomer having a OH-functional group may be used. One kind or two or more than two kinds of the same may be combined. The thusly photo-polymerized hydrogel polymer is hydrophilic and insoluble.

Since the boronic acid includes the same functional group as the polymer monomer and the polymer cross-linker, the boronic acid may be photo-polymerized together with the hydrogel. Therefore, the binding integration in the polymer of the boronic acid functional group may be enhanced without loosening the specific binding force with respect to the sugar chain which is a natural characteristic of the boronic acid. The same functional radial included in the polymer monomer, the polymer cross-linker and the boronic acid may be acryl groups, but is not limited thereto.

The polymerization reaction initiator forms radicals under the condition of ultraviolet ray, and such radicals activate the functional groups of the acryl group included in the polymer monomer for thereby inducing a radical polymerization reaction. At this time, the size of the micro passages in the hydrogel based on the concentration and ratio of the polymer monomer and the polymer cross linker. As the polymerization reaction initiator, IRGACURE® 2959 may be used, but is not limited thereto. All common photo initiators such as a mixture including alpha-hydroxy-ketone may be used. The photo-polymerization reaction has a convenience in operation since the polymerization reaction may be controlled by a start and stop of the irradiation of UV, so it is possible to synthesize and modify the polymer at a predetermined position using such a characteristic.

In the exemplary embodiment of the present disclosure, the polymer monomer may be N-(2-hydroxyethyl)acrylamide (hereinafter referred to as "HEAA"), and the polymer cross-linker may be N,N'-methylene-bisacrylamide (hereinafter referred to as "BIS").

An active radical is created by the UV (ultraviolet) irradiation and polymerization reaction initiator, and the active radical activates the acryl group of the HEAA and BIS to induce a radical polymerization reaction. The HEAA with one acryl group forms a polymer backbone, and the BIS which is a cross-linker hang two acryl groups cross-links the HEAA polymer chains. In particular, the HEAA has OH-group at its end, thus increasing hydrophillicity of the polymer. Since the HEAA induces a hydrogen binding with water molecule, it is possible to provide a natural characteristic of hydrogel which may swell by water. In addition, the OH-group serves to reduce non-specific binding (NSB) of a biological substance with respect to the polymer backbone.

The porous membrane substrate enables the absorption of the hydrogel precursor which is resolved in the solvent by the capillarity and is in the liquid state. Since it is possible to enhance convenience when managing the sample in a liquid state and handling the hydrogel with the aid of such capillarity, the porous membrane substrate is good as a support with respect to the reactive layer.

According to an exemplar embodiment of the present disclosure, the porous membrane substrate may be a saccharide detection sensor corresponding to a substrate which uses the membrane for the lateral flow assay formed of glass fibers.

For example, the porous membrane substrate may be a saccharide detection sensor corresponding to a substrate which uses the FUSION 5™ membrane (thickness is 370 μm, moisture absorption amount is 40 mg/cm$^2$ and absorption ratio is 43.9 s/4 cm). The FUSION 5™ membrane has a stable structure under the condition of most of solvents which includes an organic solvent and is capable of reducing a non-specific binding of protein with respect to the porous membrane.

According to an exemplary embodiment of the present disclosure, the boronic acid may be a saccharide detection sensor corresponding to the boronic acid with an acryl group.

The boronic acid with an acryl group may be modified between the HEAA-BIS polymers since the boronic acid joins the polymerization reaction with the aid of the acryl group. For example, (3-(acrylamido)phenylboronic acid (hereinafter, referred to as 'AAPBA'), 2-acetamido-5-acrylamidophenylboronic acid, 5-acrylamido-2-((dimethylamino)methyl)phenylboronic acid, 5-acrylamido-2-(hydroxymethyl)phenylboronic acid, 2-acrylamidophenylboronic acid, etc. may be used. The boronic acid with an acryl group forms a 3D mesh structure while the boronic acid is photo-polymerized together with the hydrogel with the aid of the acryl group, so the boronic acid may be densely integrated into the acryl hydrogel layer. Therefore, the reactive layer manufactured according to the present disclosure is characterized in that the unit cost of the support is very low as compared with the expensive metal such as gold, etc. which has been used in the conventional SAM technology, thus enhancing the economic feasibility of the production of the glycated hemoglobin detection sensor.

In addition, the method for manufacturing the saccharide detection sensor according to the present disclosure may include injecting a polymer monomer, a polymer cross-linker, a boronic acid and photo-polymerization reaction initiator into the porous membrane substrate; patterning the porous membrane substrate with a photo mask; irradiating a UV onto the patterned porous membrane substrate; washing the UV-irradiated porous membrane substrate; and drying the washed porous membrane substrate.

The step wherein the polymer monomer, the polymer cross-linker, the boronic acid and the photo-polymerization initiator are injected into the porous membrane substrate may be performed in an infrared ray drying furnace (red room) in order to avoid any interference due to natural light. The above step may be performed by a method of dripping into the porous membrane substrate a solution including a polymer monomer, a polymer cross-linker, a boronic acid, a photo-polymerization reaction initiator and a solvent thereof. In the step of patterning with the photo mask, the area of the slit of the photo mask may be matched with the size of the membrane substrate, and in case where the substrate with the FUSION 5™ membrane of which the width is 22 mm is used, the area of the slit of the photo mask may be 1 cm. The photo mask is capable of inducing the development of the hydrogel at a part of the membrane substrate by shutting off the irradiation of the ultraviolet ray with respect to the masked portion.

In the step wherein the UV is irradiated, the polymerization reaction of the polymer monomer, the polymer cross-linker and the boronic acid takes place by activating the photo-polymerization reaction initiator, wherein the intensity of the ultraviolet ray may be 0.3 to 0.4 mW/cm$^2$.

In the step of washing the membrane substrate, the polymer monomer, the polymer cross-linker, the boronic acid and the photo-polymerization reaction initiator, which are not formed into hydrogel and remain in a state of solution, are removed. As a washing solution, dimethyl sulfoxide, ethanol or distilled water may be used. As for the washing method, the membrane substrate may be impregnated in 30 minutes. As the distilled water, a third distilled water (distilled and deionized water; hereinafter referred to as 'DDW') may be used. The step of drying the washer membrane substrate may a method wherein water soluble washing liquid component is removed, and may be a method for drying at room temperature.

In the method for manufacturing a saccharide detection sensor according to an exemplary embodiment of the present disclosure, the polymer monomer may be an acrylamide derivative, and the polymer cross-linker may be an acrylamide derivative having two N functional groups (N,N'-), and the boronic acid may be a boronic acid having an acryl group.

The photo-polymerized hydrogel polymer is hydrophilic and insoluble, and since the boronic acid includes the same functional group as the polymer monomer and the polymer cross-linker, the boronic acid may be photo-polymerized together to the hydrogel for thereby forming a reactive layer. The binding integration intensity in the polymer of the boronic acid functional group may be enhancing, not losing the specific binding force with respect to the sugar chains which are the natural property of the boronic acid. The same functional group included in the polymer monomer, the polymer cross-linker and the boronic acid may be for example an acryl group, but it is not limited thereto.

The polymer cross-linker serves to adjust the durability-related reliability and cohesive force of the polymerized reactive layer by providing a cross-linking functional group. As the polymer cross-linker, the acrylamide derivative with two N functional groups (N,N'-) may be used, but it is not limited thereto, and besides the monomer having a N functional group, the monomer having an OH-functional group may be used. In addition, one kind or a combination of two or more than two kinds may be used.

In the method for manufacturing a saccharide detection sensor according to an exemplary embodiment of the present disclosure, the polymer monomer may be N-(2-hydroxyethyl)acrylamide, and the polymer cross-linker may be N,N'-methylene-bisacrylamide, and the boronic acid may be 3-(acrylamido)phenylboronic acid. With respect to the solvent of dimethyl sulfoxide, the weight ratio of N-(2-hydroxyethyl) acrylamide may be 8.00~10.00% (w/v), and the weight ratio of N,N'-methylene-bisacrylamide may be 0.40~0.50% (w/v), and the weight ratio of 3-(acrylamido) phenylboronic acid may be 0.10~2.00% (w/v), and the weight ratio of the photo-polymerization reaction initiator may be 0.05~0.14% (w/v).

N-(2-hydroxyethyl)acrylamide which joins the photo-polymerization reaction may be used as a polymer monomer which forms backbone, and N,N'-methylene-bisacrylamide may be used as a cross-linker which non-specifically polymerizes the compound through two functional groups, and the polymerization reaction initiator forms radicals under the ultraviolet ray condition, and these radicals activate the acryl group included in the acrylamide derivative for thereby inducing the radical polymerization reaction. The AAPBA also joins the polymerization reaction with the aid of the acryl group and may be modified into the acryl hydrogel without losing a specific binding force with respect to the sugar chains which are the natural property of the boronic acid. (Refer to Experimental Example 1).

With respect to the solvent of dimethyl sulfoxide, the weight ratio of N-(2-hydroxyethyl)acrylamide may be 8.00~10.00% (w/v), and the weight ratio of N,N'-methylene-bisacrylamide may be 0.40~0.50% (w/v), and the weight ratio of the photo polymerization reaction initiator may be 0.05~0.14% (w/v), and the weight ratio of the AAPBA may be 0.10~2.00% (w/v).

In the method for manufacturing a saccharide detection sensor according to an exemplary embodiment of the present disclosure, for the sake of a 3D mesh structure optimized for the use of detection of glycated hemoglobin in glycated protein, the concentrations of the AAPBA and hydrogel precursor synthesized into the reactive layer may be adjusted. The range of the optimum concentration was confirmed through the experiments. (Refer to Experimental Example 2).

The porous membrane substrate used for the method for manufacturing a saccharide detection sensor according to an exemplary embodiment of the present disclosure may be a substrate using the LFA membrane formed of glass fibers.

The porous membrane substrate may be resolved in the solvent by the capillarity for thereby allowing the hydrogel precursor, which is in a liquid state, to be absorbed. Since it is possible to enhance any convenience when handling the management of the sample which is in a liquid state and the hydrogel with the aid of the capillarity, the porous membrane substrate may be proper as a support with respect to the relative layer.

For example, the porous membrane substrate may be a saccharide detection sensor corresponding to a substrate which uses the FUSION 5™ (thickness is 370 μm, moisture absorption amount is 40 mg/cm$^2$ and absorption ratio is 43.9 s/4 cm). The FUSION 5™ membrane has a stable structure under the condition of most of solvents which includes an organic solvent and is capable of reducing a non-specific binding of protein with respect to the porous membrane. (Refer to Exemplary Embodiment 2).

In addition, the method for detecting glycated hemoglobin according to the present disclosure includes mixing the glycated hemoglobin and horseradish peroxidase (hereinafter referred to as 'HRP') and reacting the mixed glycated hemoglobin and the horseradish peroxidase with the saccharide detection sensor based on an exemplary embodiment of the present disclosure; washing the non-reactive protein after reaction; inducing a color development by dripping a chromogen working solution including a chromogen and a substrate with respect to the HRP onto the sensor for detecting saccharide; and digitizing and outputting the degree of the color development.

The step of mixing the glycated hemoglobin and the HRP and reacting the mixed glycated hemoglobin and the horseradish peroxidase with the saccharide detection sensor may be a step for competitively reacting the boronic acid and the glycated hemoglobin and the HRP. For example, it is possible to induce a competitive cis-diol binding reaction between the glycated hemoglobin which is a glycated protein and the HRP by using the porous membrane substrate at which the AAPBA-acryl hydrogel are fixed, which are synthesized using the HEAA, BIS and AAPBA as materials. The glycated hemoglobin which is a detection target substance, is mixed with the HRP which is a signal generation substance and is processed into a reaction layer, and two kinds of the substances are competitively bound with respect to the boronic acid-hydrogel.

In the step of washing non-reactive protein, it is possible to remove noise which may occur when measuring the amount of protein reaction through the washing after reaction. For example, in order to remove the non-reactive HRP, the PBS solution, etc. which resolves the HRP, may be used as a washing liquid.

The step of inducing color development by dripping a chromogen working solution including a substrate and chromogen with respect to the HRP onto the sensor for detecting saccharide, is a step wherein a product manufactured by the reaction between the HRP and the substrate reacts again with the chromogen and forms a color. This procedure is to indirectly quantify the concentration of the glycated hemoglobin based on the phenomenon where the higher the concentration of the glycated hemoglobin, the lower the criteria of the HRP enzyme color development reaction with respect to the color development substrate. If the color development reaction of the chromogen including the substrate following the competitive binding of the glycated hemoglobin and the HRP, it becomes possible to obtain a color development signal which is in reverse proportion to the concentration of the hemoglobin. The concentration of the glycated hemoglobin may be calculated by analyzing any change in such a color development signal.

The substrate of the HRP enzyme reaction may be reacted into hydrogen peroxide, and the chromogen may be selected from the group consisting of 3,3',5,5'-tetramethylbenzidine (hereinafter referred to as 'TMB'), o-phenylenediamine dihydrochloride (hereinafter referred to as 'OPD'), 2,2'-azinobis [3-ethylbenzothiazoline-6-sulfonic acid]-diammonium salt (hereinafter referred to as 'ABTS'), 3,3'-diaminobenzidine tetrahydrochloride (hereinafter referred to as 'DAB'), SAT-3 (analog of o-tolidine), N-ethyl-N-(2-hydroxy-3-sulfopropyl)-3-methoxyaniline sodium salt dihydrate, N-ethyl-N-(3-sulfopropyl)-3-methoxyaniline sodium salt monohydrate, N-ethyl-N-(3-sulfopropyl)aniline, sodium salt, N-ethyl-N-(2-hydroxy-3-sulfopropyl)-3,5-dimethoxyaniline sodium salt, N-(2-hydroxy-3-sulfopropyl)-3,5-dimethoxyaniline sodium salt), N,N-Bis(4-sulfobutyl)-3,5-dimethylaniline disodium salt, N-ethyl-N-(2-hydroxy-3-sulfopropyl)-3,5-dimethylaniline sodium salt monohydrate, N,N-Bis(4-sulfobutyl)-3-methylaniline disodium salt, N-ethyl-N-(2-hydroxy-3-sulfopropyl)-3-methylaniline sodium salt dihydrate and N-ethyl-N-(3-sulfopropyl)-3-methylaniline sodium salt monohydrate.

For example, if the glycated hemoglobin of various concentration and the HRP with a predetermined concentration are mixed and reacted on the glycated hemoglobin detection sensor including the boronic acid-modified hydrogel and the membrane substrate, the glycated hemoglobin and the HRP are competitively bound with respect to the BA reaction group. At this time, if the concentration of the glycated hemoglobin is higher, the glycated hemoglobin with higher concentration competitively competes with the HRP, and as a result, the binding of the HRP and the BA is inhibited. After the non-reactive protein is removed through the washing procedure, color development is induced by the TMB sample being treated. The competition between the glycated hemoglobin and the HRP induces the reduction of the HRP binding degree, After all, the higher the concentration of the glycated hemoglobin, the lower the degree of the HRP enzyme color development reaction with respect to the TMB substrate. The degree of the color development obtained from the decreased color development reaction is digitized, outputted and analyzed, so the concentration of the glycated hemoglobin included in the finally processed sample may be estimated. In a corresponding TMB color development reaction, the color development is proceeded by the product made by the HRP and the hydrogen peroxide as substrate, and the typical concentration of the TMB is 0.2~0.8 mg/ml, and the hydrogen peroxide may be used within a concentration range of 0.02~0.05%.

Besides the TMB, the substances such as OPD, ABTS, DAB or SAT-3 may be used as the chromogen. In case of the OPD, the OPD may be used under the condition of the concentration of 0.5~1.0 mg/ml and the hydrogen peroxide of 0.03%. Besides the above matter, as the substances which is bound with 4-aminoantipyrin (4-AAP) and show color development, the chromogens called Trinder's reagent such as (N-ethyl-N-(2-hydroxy-3-sulfopropyl)-3-methoxyaniline sodium salt dihydrate, N-ethyl-N-(3-sulfopropyl)-3-methoxyaniline sodium salt monohydrate, N-ethyl-N-(3-sulfopropyl)aniline, sodium salt, N-ethyl-N-(2-hydroxy-3-sulfopropyl)-3,5-dimethoxyaniline sodium salt, N-(2-hydroxy-3-sulfopropyl)-3,5-dimethoxyaniline sodium salt), N,N-Bis(4-sulfobutyl)-3,5-dimethylaniline disodium salt, N-ethyl-N-(2-hydroxy-3-sulfopropyl)-3,5-dimethylaniline sodium salt monohydrate, N,N-Bis(4-sulfobutyl)-3-methylaniline disodium salt, N-ethyl-N-(2-hydroxy-3-sulfopropyl)-3-methylaniline sodium salt dihydrate and N-ethyl-N-(3-sulfopropyl)-3-methylaniline sodium salt monohydrate) may be used.

Figure 13:
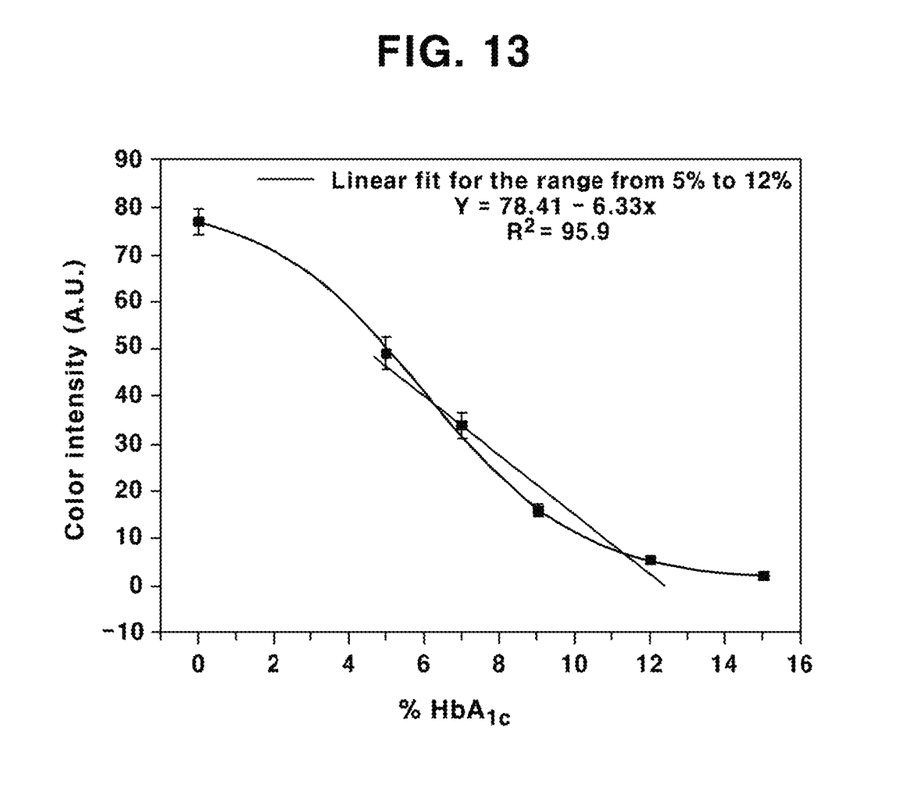
FIG. 13 is a calibration curve illustrating a result of a quantitative analysis of glycated hemoglobin based on a method for detecting glycated hemoglobin according to the present disclosure.

The step of digitizing and outputting the degree of the color development may include photographing with a digital camera the image which has a color development by the TMB solution; loading the photographed image into the Adobe Photoshop program; selecting the portion of the color development on the Photoshop program and moving to "analysis tool"; selecting "blue Pixel analysis" after selecting "RG mode in the Photoshop program; and recording the average amount of light measured by "Blue Pixel analysis". It is quantified the detected glycated hemoglobin based on the method for detecting the glycated hemoglobin. At this time, it is possible to compensate for any inference due to external light by using the chromaticity standard corresponding to "Internal Reference". FIG. 13 is a view illustrating a result of the quantitative analysis on the glycated hemoglobin with a calibration curve based on the method for detecting the glycated hemoglobin according to the present disclosure.

In addition, the step of mixing the glycated hemoglobin and the HRP and reacting using the saccharide detection sensor is characterized in that onto the saccharide detection sensor, a solution obtained by mixing at a volumetric ratio of 1:1 the HRP and the glycated hemoglobin resolved in the PBS solution at a concentration of 1 to 10 µg/ml is dripped by 1 to 100 µl and is reacted for 10 to 600 seconds. (Refer to Experimental Examples 3 and 4).

The step of washing the non-reactive protein may include a step wherein the reactive layer is washed twice using a washing solution of pH 8.0 by resolving TX-100 of 0.1% and PEG (MW=3400) of 0.01% in 50 mM of Tris buffer solution, and the reactive layer is washed once using a washing solution of pH 7.4 by resolving 0.1% of TX-100 and 0.01% of PEG (MW=3400) in 50 mM of the PBS buffer solution. At this time, the PBS solution in which the HRP is resolved, may have pH 7.4 by resolving 0.1% of TX-100 and 0.01% of PEG (MW-3400) in 50 mM of the PBS buffer solution.

As in the exemplary embodiment 3 below, the method for detecting the glycated hemoglobin according to the present disclosure has showed a result wherein the present disclosure has satisfied the clinical glycated hemoglobin diagnosis ranges of both the normal person and the diabetes mellitus patient.

[Exemplary Embodiment 1]

Synthesis of Boronic Acid-Hydrogel

The photo-polymerization reaction-based hydrogel was synthesized by mixing the monomer, the cross-linker and the polymerization reaction initiator. The radical polymerization reaction between the acryl groups existing in the molecular structures of the precursor may occur through the productions of the radicals of the polymerization reaction initiator in such a way that 10% of the HEAA used as the monomer, 0.5% (a ratio of 20:1 as compared with the monomer) of the BIS used as the cross-linker and 0.1% of the polymerization reaction initiator were melted and mixed in the DMSO solution under dark condition and the irradiation of UV. The photo-polymerization reaction has a convenience in operation in the way that the polymerization reaction may be controlled by the start-stop way of the irradiation of UV, so it is possible to synthesize and modify the polymers only at a predetermined position using the above operation. In case where the hydrogel is synthesized, since the hydrogel is a solid substance, the content does not flow down even through the test tube is turned upside down. In case where the synthesis is not performed, the hydrogel remains in a water soluble state. The synthesizing state was judged while visually checking any change in the physical properties.

Figure 1:
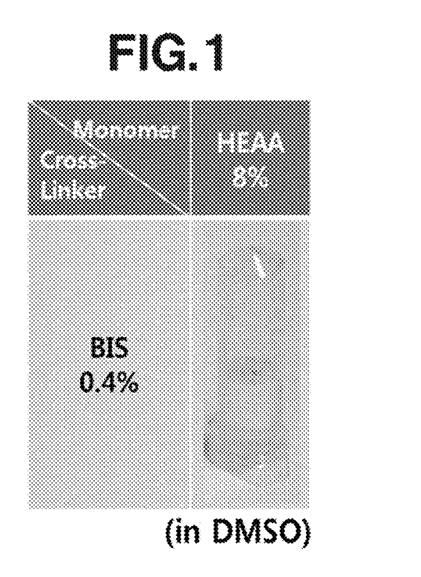
FIG. 1 is a view illustrating a result of hydrogel synthesis of a reactive layer according to an exemplary embodiment of the present disclosure.

As a result of the experiment, it was possible to check that the hydrogel was synthesized as illustrate in FIG. 1. FIG. 2 shows the molecular structures of the HEAA, BIS, polymerization reaction initiator and AAPBA which are selected as the precursors for the synthesis of the hydrogel. FIG. 2 shows the molecular structures of the hydrogel (the hydrogel synthesized using the HEAA, BIS and AAPBA as the precursors is called 'HEAA-BIS-AAPBA hydrogel') synthesized through the above procedures.

[Exemplary Embodiment 2]

Membrane Substrate at which Boronic Acid-Hydrogel is Fixed

If the porous membrane substrate is used so as to fix the reactive layer synthesized with the boronic acid-modified hydrogel, it is possible to simply and efficiently perform the washing procedure which is necessary to a bio-sensing with the aid of the capillarity that the porous membrane has.

The LFA (Lateral Flow Assay) used as a representative of the porous membranes may perform a movement and washing of the sample by using the capillarity of the membrane which forms the LFA strip without using any external fluid transfer pump, a flow path, etc.

Figure 3:
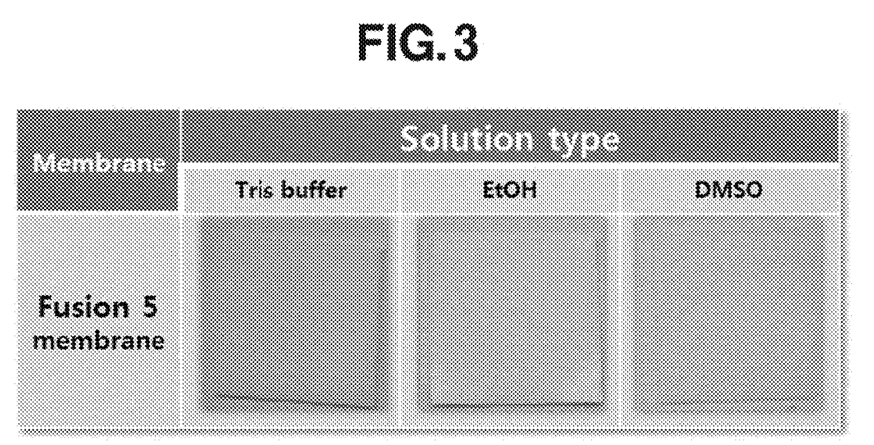
FIG. 3 is a view illustrating a result of a comparison of solvent safety of a FUSION 5™ membrane according to an exemplary embodiment of the present disclosure.

Since the HEAA-BIS-AAPBA hydrogel may be synthesized under the DMSO solution condition, the porous membrane substrate which is used for the above should maintain the stable shape and structure under the DMSO solution condition. The Tris buffer (aqueous phase), the ethanol and the DMSO were treated respectively with respect to the FUSION 5™ membrane, and as a result of the observation on any change, as illustrated in FIG. 3, it was confirmed that the FUSION 5™ membrane has showed the stable structure under all the solvent conditions.

Besides the structural stability of the membrane, the non-specific binding state of the protein with respect to the membrane is a very important consideration matter in terms of the bio-sensing. For a confirmation thereof, the HRP which will be used as a signaling substance with respect to the FUSION 5™ membrane was treated, and the degree of the TMB color development reaction was observed. There were prepared an experimental group wherein nothing was treated for the FUSION 5™ membrane and an experimental group wherein the blocking was conducted using the BSA (6%) and the PEG (7%), and with respect to the FUSION 5™ membrane, 10 µg/ml of the HRP was reacted for 5 minutes with respect to the FUSION 5™ membrane and was washed, and the degree of the color development was checked after treating the TMB solution.

Figure 4:
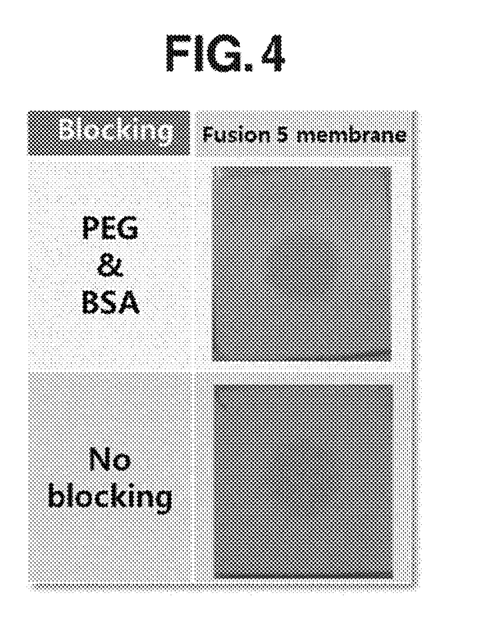
FIG. 4 is a view illustrating a result of the confirmation of a nonspecific binding state of HRP with respect to a FUSION 5™ membrane according to an exemplary embodiment of the present disclosure.

As a result illustrated in FIG. 4, no color development by the HRP was observed even in the experimental group wherein any blocking procedure was not performed.

Therefore, the FUSION 5™ membrane which has maintained a stable structure under the DMSO solution condition and in which the NSB with respect to the HRP which is a signaling substance was not observed, was selected as the membrane substrate according to an exemplary embodiment of the present disclosure.

EXPERIMENTAL EXAMPLE 1

Confirmation of Binding Force with Respect to Glycated Protein of the Reactive Layer Synthesized with Boronic Acid-Hydrogel In order to check any effects of the saccharide detection effects according to an experimental embodiment of the present disclosure, whether or not the glycated protein was efficiently bound to the substance of the reactive layer was checked. The HRP which is a representative glycated protein and an oxidation-reduction enzyme capable of inducing the color development reaction through the enzyme reaction itself was reacted with the substance of the reactive layer by concentration difference, and the level of the generating color development signal was analyzed, and the binding power of the saccharide protein with respect to a corresponding reactive layer was checked.

Figure 5:
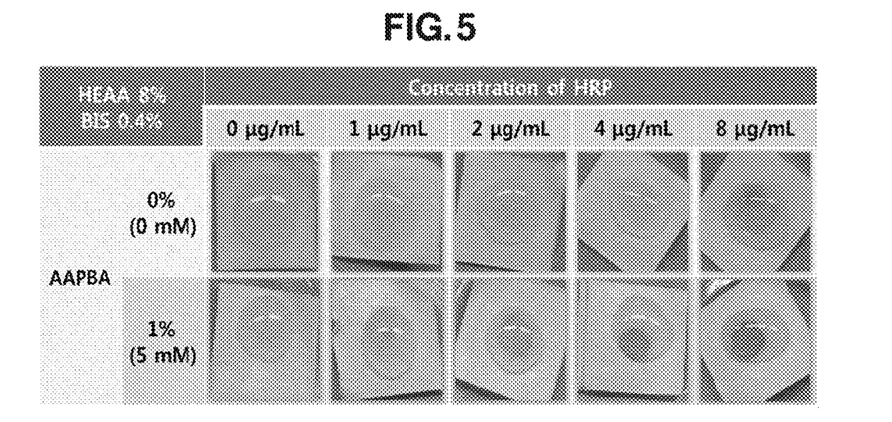
FIG. 5 is a view illustrating a result of the confirmation of a HRP binding state with respect to a boronic acid-hydrogel according to an exemplary embodiment of the present disclosure.

The HRP (0~8 µg/ml) by concentration difference was reacted with respect to the porous membrane substrate at which the hydrogel was fixed, and the TMB color development reaction was induced. As a result illustrated in FIG. 5, in case where the boronic acid was treated, it was observed that the intensity of the color development of the enzyme color development reaction was increased in proportion to the concentration of the HRP. In contrast to that, in the control group wherein the boronic acid was not present, the color development was not observed to the HRP concentration level of 4 µg/ml, and it was observed that any non-specific binding such as hydrophobic interaction was not made in the HRP with respect to the synthesized hydrogel. That the degree of the color development was largely changed depending on the presence of the boronic acid proved that the selective binding of the saccharide protein was is made by the boronic acid, and it was confirmed that the HEAA-BIS-AAPBA hydrogel could be used for the sake of the measurement of the glycated hemoglobin according to the present disclosure. In the following experiments, the most strong color development was observed, and the HRP concentration of 4 µg/ml where the size of the NSB was smallest were adopted as a basic condition.

EXPERIMENTAL EXAMPLE 2

Optimization of Synthesis Condition of Reactive Layer of Boronic Acid-Modified Hydrogel For the sake of the efficient detection of the glycated hemoglobin, the adjustment of the density of the polymer chains and the integration degree of the boronic acid group are indispensable in the course of the synthesis of the HEAA-BIS-AAPBA hydrogel. For this, some experiments were performed so as to synthesize the reactive layer which may effectively collect the glycated hemoglobin and provide the optimum optical signals by adjusting the concentrations of the HEAA, BIS and AAPBA.

A. Selection of Concentration of Polymer Monomer Used in Boronic Acid-Modified Hydrogel Reactive Layer Synthesis The HEAA-BIS-AAPBA hydrogel has HEAA and BIS as major components, and hydrogel is formed through the cross-linking reaction thereof. At this time, if the hydrogel is formed too densely, the protein such as the HRP and glycated hemoglobin may not penetrate into the hydrogel. If the hydrogel is synthesized at too low density, the degree of the boronic acid modification is lowered, so the high signal yield may be impossible or the hydrogel itself may not be formed. In order to search for the optimum HEAA-BIS concentration, the boronic acid-hydrogel was synthesized by changing the concentration of the HEAA in a range of 6% to 14%. All the hydrogel synthesis was performed on the FUSION 5™ membrane, and the concentration of the BIS was fixed at 1/20 of each HEAA concentration. The AAPBA was designed under both the conditions of 0% and 1%. In the 0% AAPBA, the experiment was prepared so that the NSB signal could be observed. 4 µg/ml of the HRP was reacted for 5 minutes with respect to the porous membrane substrate at which each HEAA-BIS-AAPBA was fixed, and the TMB was treated after washing, and the intensities of the color development were compared.

Figure 6:
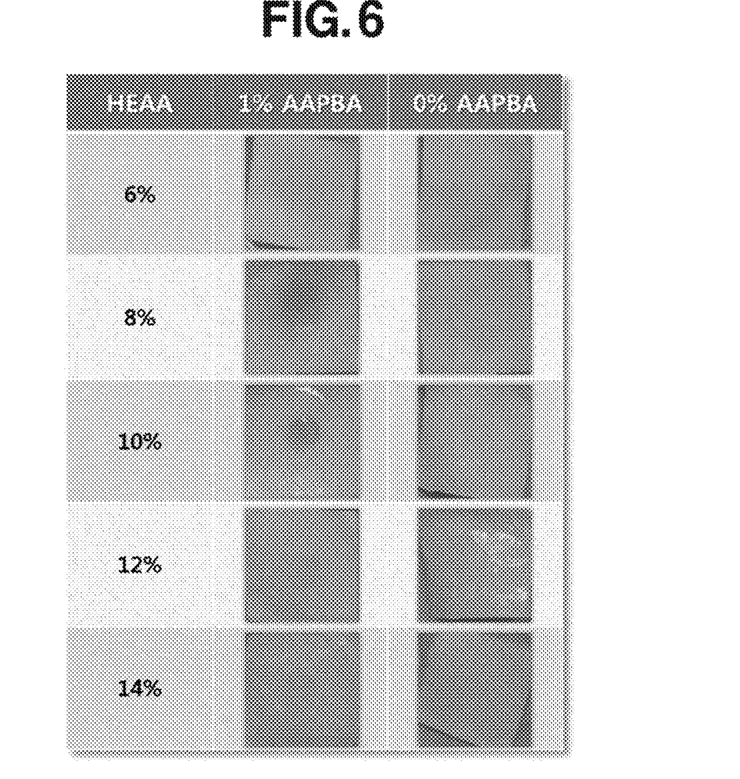
FIG. 6 is a view illustrating a change in a HRP color development signal based on a HEAA concentration in a boronic acid-hydrogel according to an exemplary embodiment of the present disclosure.

As illustrated in FIG. 6, it was possible to see that the color development reaction was very weak by the HRP at the HEAA concentration of above 10%. This means that if the HEAA of above 10% was present, the hydrogel was synthesized too densely, and the spreading and binding reaction induction of the HRP didn't take place well. On the contrary, at the 8% HEAA, the very strong color development reaction was observed, which means that the spreading of the HRP and the binding with respect to the BA were conducted at high levels, respectively. At the 6% HEAA concentration, the hydrogel was formed too sloppy, so it was confirmed that there were almost little hydrogel molecule in the membrane. Based on the above result, it was decided that the conditions of HEAA of 8% and BIS of 0.4% will be adopted to the following experiments.

B. Optimization of Boronic Acid Concentration Used for the Synthesis of Boronic Acid-Modified Hydrogel Reactive Layer In order to efficiently bind more glycated protein, the boronic acid molecules should be present with high concentration inside of the hydrogel. In order to check the concentration of the boronic acid for the sake of efficient saccharide detection, various concentration of AAPBA (0, 0.0001, 0.001, 0.01, 0.1, 1, 2, 3, 4, 5%) were prepared and added to HEAA-BIS (8%, 0.4%) respectively, for thereby synthesizing the HEAA-BIS-AAPBA hydrogel. All the reactions were performed on the FUSION 5™ membrane, after the HRP of 4 µg/ml was reacted for 5 minutes, and the TMB was treated, and the color development intensities were compared.

Figure 7:
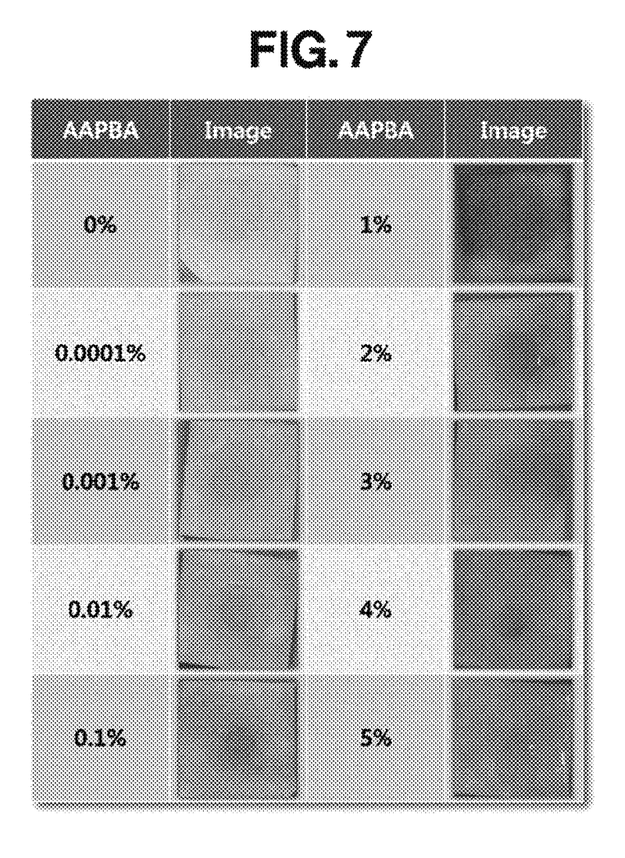
FIG. 7 is a view illustrating a change in a HRP color development signal based on an AAPBA concentration in a boronic acid-hydrogel according to an exemplary embodiment of the present disclosure.

As illustrated in FIG. 7, it was possible to confirm that the intensities of the color development reactions by the HRP were in proportion to the concentration of the AAPBA up to the concentration of 0~1% of the AAPBA, and a phenomenon was observed that after the above concentrations, the intensities of the color development reactions were gradually decreased. It is judged that the color development signals at the high BA concentration (above 2%) were decreased since the penetration of the HRP was inhibited since the density of the hydrogel was increased depending on the increase of the AAPBA concentration which is similar with the case of the high concentration of the HEAA. At the condition of the AAPBA of 1% concentration, the color development signal was highest, and in the following experiments, the HEAA-BIS-AAPBA hydrogel was synthesized under the corresponding concentration condition and was used.

EXPERIMENTAL EXAMPLE 3

Optimization of Horseradish Peroxidase (HRP) Signal Generation Condition of Boronic Acid-Modified Hydrogel The following experiments were performed as follows in order to recognize the reaction amount and the reaction time of the HRP which is used in the method for detecting glycated hemoglobin according to an exemplary embodiment of the present disclosure.

If the reaction time takes longer in the cis-diol reaction of the boronic acid and the HRP, more HRPs are bound for thereby obtaining higher signals, but such reaction time entails the increase of the non-binding of the non-specific HRP, thus inhibiting the yield of accurate signals. For this reasons, the optimum signal substance (HRP) and reaction time were selected to obtain higher color development signals while minimizing the NSB.

The HEAA-BIS-AAPBA (each 8%, 0.4%, 1%) hydrogel was formed on the FUSION 5™ membrane, and the HRP of 4 µg/ml was reacted for 10 seconds, 30 seconds, 1 minute, 3 minutes, 5 minutes and 10 minutes respectively, and the TMB was treated, and the color development intensities were compared. For the control group, the membrane on which the AAPBA was not treated was used.

Figure 8:
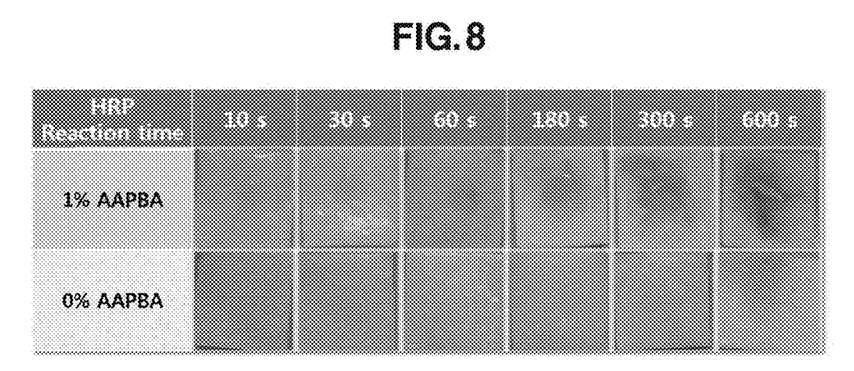
FIG. 8 is a view illustrating the optimum HRP reaction time.

As a result of the experiment, the high color development and the low NSB signal were observed in the experiment group in which the HRP was reacted for 5 minutes. (Refer to FIG. 8). In case where the reaction was performed for 10 minutes, the color development reaction with the highest intensity was observed, and a relatively high level of color development by the NSB was observed in the non-boronic acid experimental group.

EXPERIMENTAL EXAMPLE 4

Figure 9:
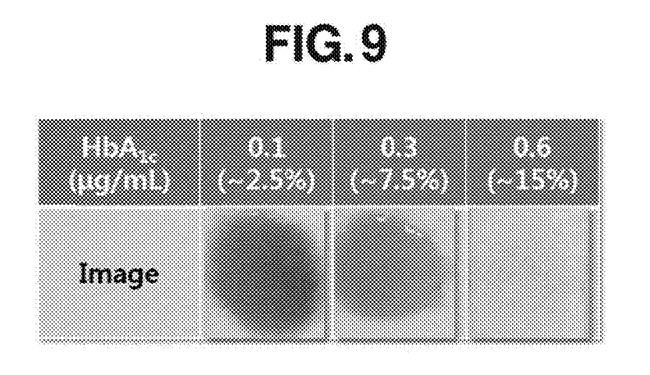
FIG. 9 is a view illustrating a change in a HRP color development signal based on the concentration of glycated hemoglobin.

Result of Horseradish Peroxidase (HRP) Signal Generation of Boronic Acid-Modified Hydrogel FIG. 9 is a view illustrating a result of the color development levels when the HRP of the same amount (4 µg/ml) and the glycated hemoglobin sample (only the glycated hemoglobin exists) of three kinds of concentrations (0.1, 0.3, 0.6 µg/ml) were mixed and treated on the HEAA-BIS-AAPBA hydrogel.

As a result of the experiment, It was observed that the color development by the HRP was decreased when the concentration of the glycated hemoglobin increased by the competitive reaction between the glycated hemoglobin and the HRP. This result represents that the reactive layer for the glycated hemoglobin detection according to the present disclosure may be actually applied to the glycated hemoglobin quantitative analysis, and the quantitative analysis of the glycated hemoglobin was performed based on the above result.

Figure 10:
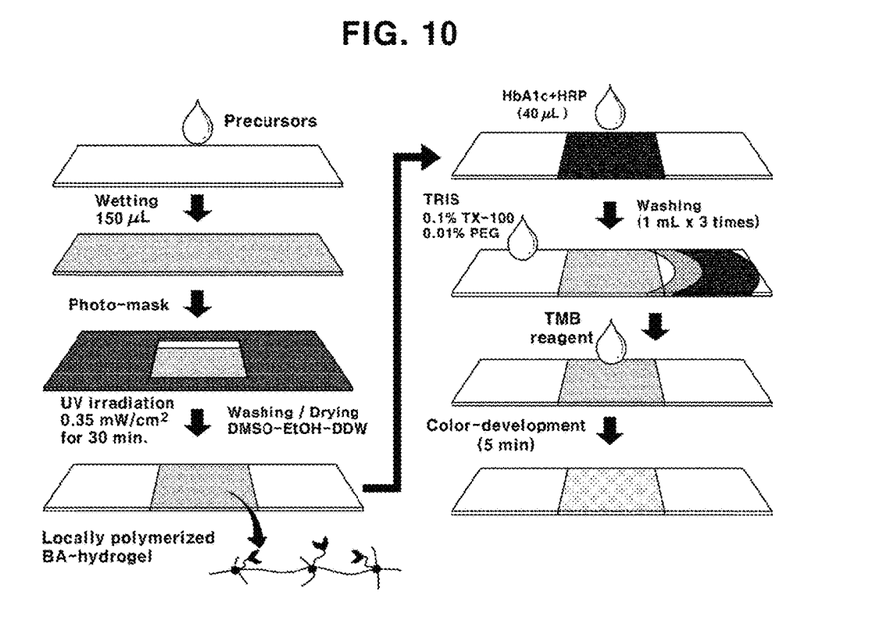
FIG. 10 is a view illustrating a synthesis method of a boronic acid-hydrogel and an analysis method of glycated hemoglobin using the same according to an exemplary embodiment of the present disclosure.

Quantitative Analysis of Glycated Hemoglobin Using Boronic Acid-Modified Hydrogel Reactive Layer The method for detecting glycated hemoglobin according to an exemplary embodiment of the present disclosure (refer to FIG. 10) includes mixing the glycated hemoglobin and the HRP and reacting on the glycated hemoglobin detection sensor, so it is possible to enhance the quantitative efficiency of the glycated hemoglobin through the competitive reaction between the glycated hemoglobin and the HRP.

In terms of the concentration-dependent color development signal yield of the glycated hemoglobin, the most important matter which should be considered is the mixing ratio of the glycated hemoglobin and the HRP. The method for detecting the glycated hemoglobin according to an exemplary embodiment of the present disclosure is characterized in that the final concentration ratios of the Hb and HRP which may provide the optimum signals while competing on the HEAA-BIS-AAPBA hydrogel reactive layer are three ratios in the following Table 1.

TABLE 1

| Hb:HRP | Ratios |
|---|---|
| 40 μg/ml:4 μg/ml | 10:1 |
| 4 μg/ml:4 μg/ml | 1:1 |
| 4 μg/ml:40 μg/ml | 1:10 |

In case of the total hemoglobin (hereinafter referred to as 'Hb') in which the glycated hemoglobin is mixed, it was prepared in such a way that only the hemoglobin was separated from the actually collected blood and purified, and the reagent of the glycated hemoglobin was added. It was adjusted to produce the glycated hemoglobin concentration of 5% and 12%. Various ranges of the total protein concentrations of the corresponding Hb sample were prepared, and such concentrations were diluted using the PBS. 8 μg/ml and 80 μg/ml of the concentrations were prepared using the 500 mM PBS solution (0.1% TX-100, 0.01% PEG). The Hb sample and the HRP sample were mixed at the same volume ratio (1:1).

Each sample was reacted for 5 minutes on the porous membrane substrate at which the HEAA-BIS-AAPBA hydrogel was fixed. The residual non-reactive substances were removed using the washing buffer solution (50 mM Tris, pH 8, 0.1% TX-100, 0.01% PEG), and the color development reaction was induced using the TMB solution, and the results were compared.

Figure 11:
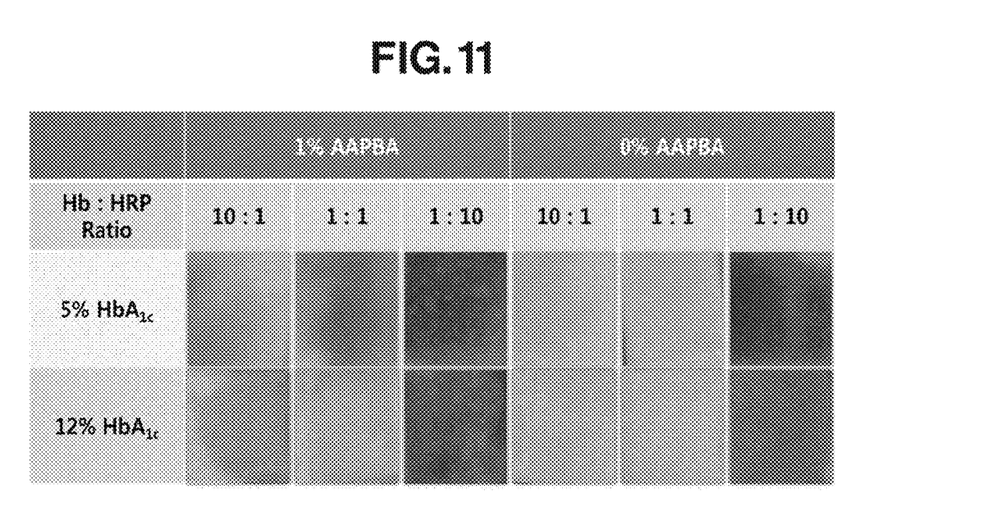
FIG. 11 is a view illustrating a change in a HRP color development signal based on a concentration ratio of a HRP/glycated hemoglobin.

As illustrated in FIG. 11, there were differences in all the color developments under the condition where the concentration ratios of the Hb and the HRP were 10:1, 1:1 and 1:10, and it was observed that the color development of the condition 1:1 had the highest intensity. It was also observed that there was a significant difference in the color development intensity in case of the ratio 1:1 of the Hb and the HRP by comparing the results of 5% and 12% glycated hemoglobin. In the experiment where the HRP had the final concentration of 40 μg/ml, the high color development reactions by the NB were observed irrespective of the concentration of the Hb. Under the condition which was performed in the control group and where there was not the boronic acid, there were not any color development in case where the final concentration of the HRP was 4 μg/ml, and it was observed that there was the high color development in case where the final concentration was 40 μg/ml.

In the following experiments, the measurements were performed based on the glycated hemoglobin concentration by assuming that the final concentration ratios of the Hb and the HRP were "Hb 4 μg/ml: HRP 4 μg/ml (1:1)".

8 μg/ml Hb and 8 μg/ml HRP were mixed at the volumetric ratio of 1:1 until the final concentrations of 4 μg/ml was obtained respectively. Each Hb sample was prepared in order for the glycated hemoglobin concentration of 5, 7, 9, 12, 15% to be obtained. Since the 0% glycated hemoglobin sample is theoretically impossible, the PBS of the same volume was mixed with the HRP for use. The prepared Hb-HRP mixed sample was reacted for 5 minutes on the surface of the reactive layer synthesized with the HEAA-BIS-AAPBA hydrogel, and the reacted substance was washed three times with the washing buffer solution, and the TMB color development reaction was induced. The color-formed optical signal was measured using the digital camera afterward 5 minutes after the TMB reaction, and the recorded images were analyzed using the Photoshop program, and the luminous intensity of the blue pixel of the portion of the color development was quantified.

Figure 12:
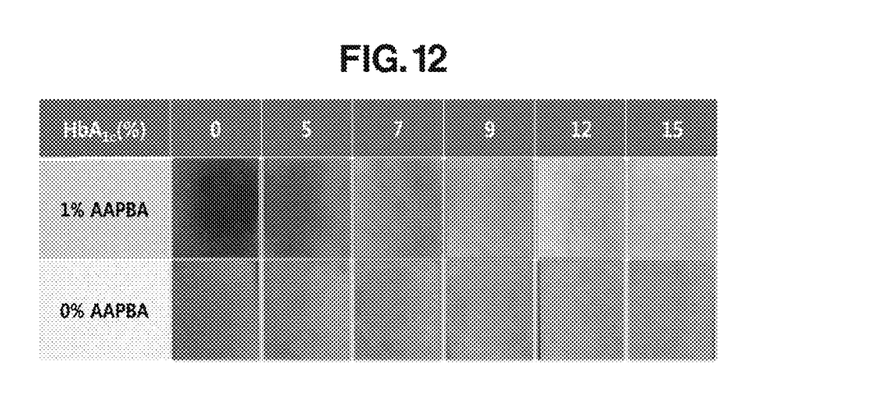
FIG. 12 is a view illustrating a result of a quantitative analysis of a glycated hemoglobin based on a method for detecting glycated hemoglobin according to the present disclosure.

As illustrated in FIG. 12, it was observed that if the concentration of the glycated hemoglobin increased, the intensity of the color development was weakened. In case of 0% sample where the glycated hemoglobin was not provided, the highest color development was observed. In case of the 15% glycated hemoglobin sample, it was observed that there was little color development. The color development was not observed in the hydrogel where the boronic acid used as the control group was not treated. A weak signal was observed only in the 0% experimental group. It was confirmed from the above result that the boronic acid would be applied to the glycated protein analysis, and it was also confirmed that the glycated hemoglobin which is the biomarker of the diabetes mellitus would be quantitatively analyzed through the competitive reaction. In order to more quantitatively check the color development, the blue pixel luminous intensity was measured using the Photoshop software, and the calibration curve of the glycated hemoglobin was made as illustrated in FIG. 15.

As a result of the experiments which were performed four times repeatedly, the coefficient of variation (COV=SD/mean) of the method for detecting the glycated hemoglobin using the reactive layer for detecting the glycated hemoglobin according to the present disclosure was about 7%, and it was confirmed that the linear detection range was formed in the section of 5-12% of the glycated hemoglobin. The slope of the straight trend line in a corresponding linear detection range was −6.3, and the reliability ($R^2$) was 0.96. The sample binding reaction time with respect to the reactive layer was 5 minutes, and the actual color development reaction was finished within 5 minutes.

According to the method for detecting the glycated hemoglobin using the reactive layer for detecting the glycated hemoglobin of the present disclosure, it was possible to sensitively detect the change in the concentration of the glycated hemoglobin around 7% which is most importantly required for the sake of diagnosis of diabetes mellitus (5%~12% straight line section slope=6.3), and the coefficient of variation (COV=SD/mean) of 7% was obtained. The total glycated hemoglobin detection reaction time except for the washing procedure was 10 minutes (sample reaction 5 minute+color development reaction 5 minutes). Additional fluid control equipment was not necessary due to the capillarity of the membrane. The above results are summarized and shown in the following Table 1.

TABLE 2

| Evaluation Items | Targets | Results obtained |
|---|---|---|
| Precision of $HbA_{1c}$ sensing | COV = 7% | COV < % (use of actual blood) |
| Linearity (detection Range) | 3~15% $HbA_{1c}$ | 5%~12% $HbA_{1c}$ (3%~15%) |

TABLE 2-continued

| Evaluation Items | Targets | Results obtained |
|---|---|---|
| Sensitivity of output signal | 0.05 ABS/% $HbA_{1c}$ | 6.33AU/% $HbA_{1c}$ (5~12% range) |
| Final sample reaction time | Within 10 minutes | Competition reaction |
| Signal detection time | | TMB reaction 5 min |

[Result of Detection Quantitative Evaluation of Glycated Hemoglobin Using Synthesized Boronic Acid-Hydrogel Reactive Layer]

As the present disclosure may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

The invention claimed is:

1. A sensor for detecting a saccharide, the sensor comprising:
   a reactive layer comprising a hydrogel having a boronic acid-modified three-dimensional mesh structure; and
   a porous membrane substrate fixed with the reactive layer,
   wherein the hydrogel comprises 8.00%-10.00% (w/v) of N-(2-hydroxyethyl) acrylamide, 0.40%-0.50% (w/v) of N,N'-methylene-bisacrylamide, and 0.10%-2.00% (w/v) of 3-(acrylamido) phenylboronic acid.

2. The sensor of claim 1, wherein the saccharide is a saccharide portion of glycated protein or glucose.

3. The sensor of claim 2, wherein the glycated protein is glycated hemoglobin ($HbA_{1c}$).

4. The sensor of claim 1, wherein the porous membrane substrate is a substrate using a membrane for a LFA (Lateral Flow Assay) formed of glass fibers.

5. A method for manufacturing the sensor of claim 1, the method comprising:
   injecting a polymer monomer, a polymer cross-linker, boronic acid, and a photo-polymerization reaction initiator into the porous membrane substrate;
   patterning the porous membrane substrate with a photomask;
   irradiating UV (ultraviolet) onto the patterned porous membrane substrate;
   washing the UV-irradiated porous membrane substrate; and drying the washed porous membrane substrate,
   wherein the polymer monomer is N-(2-hydroxyethyl) acrylamide, the polymer cross-linker is N,N'-methylene-bisacrylamide, and the boronic acid is 3-(acrylamido)phenylboronic acid, and wherein the N-(2-hydroxyethyl)acrylamide, the N,N'-methylene-bisacrylamide, the 3-(acrylamido)phenylboronic acid and the photo-polymerization reaction initiator are mixed in a dimethyl sulfoxide solvent prior to injection at a weight ratio of 8.00-10.00% (w/v) of the N-(2-hydroxyethyl)acrylamide, 0.40-0.50% (w/v) of the N,N'-methylene-bisacrylamide, 0.10-2.00% (w/v) of the 3-(acrylamido)phenylboronic acid, and 0.05-0.14% (w/v) of the photo-polymerization reaction initiator.

6. The method of claim 5, wherein the porous membrane substrate is a substrate using a membrane for a LFA (Lateral Flow Assay) formed of glass fibers.

7. A method for detecting glycated hemoglobin, the method comprising:
   mixing and reacting glycated hemoglobin and horseradish peroxidase on the sensor of claim 1;
   washing non-reactive protein after the reacting of the mixed glycated hemoglobin and horseradish peroxidase;
   inducing a color development by dripping a chromogen working solution including a chromogen and a substrate with respect to the horseradish peroxidase onto the sensor;
   digitizing a degree of the color development; and
   outputting the digitized degree corresponding to a concentration of the detected glycated hemoglobin.

8. The method of claim 7, wherein the substrate is hydrogen peroxide, and the chromogen is any one selected from the group consisting of 3,3',5,5'-tetramethylbenzidine, o-phenylenediamine dihydrochloride, 2,2'-azinobis[3-ethylbenzothiazoline-6-sulfonic acid]-diammonium salt, 3,3'-diaminobenzidine tetrahydrochloride, SAT-3 (analog of o-tolidine), N-ethyl-N-(2-hydroxy-3-sulfopropyl)-3-methoxyaniline sodium salt dihydrate, N-ethyl-N-(3-sulfopropyl)-3-methoxyaniline sodium salt monohydrate, N-ethyl-N-(3-sulfopropyl)aniline, sodium salt, N-ethyl-N-(2-hydroxy-3-sulfopropyl)-3,5-dimethoxyaniline sodium salt, N-(2-hydroxy-3-sulfopropyl)-3,5-dimethoxyaniline sodium salt), N,N-Bis(4-sulfobutyl)-3,5-dimethylaniline disodium salt, N-ethyl-N-(2-hydroxy-3-sulfopropyl)-3,5-dimethylaniline sodium salt monohydrate, N,N-Bis(4-sulfobutyl)-3-methylaniline disodium salt, N-ethyl-N-(2-hydroxy-3-sulfopropyl)-3-methylaniline sodium salt dihydrate and N-ethyl-N-(3-sulfopropyl)-3-methylaniline sodium salt monohydrate.

9. The method of claim 7, wherein the mixing and reacting the glycated hemoglobin and the horseradish peroxidase comprises:
   dropping 1 to 100 µl of a solution, which is prepared by mixing and resolving the horseradish peroxidase and the glycated hemoglobin at a volumetric ratio of 1:1 in a PBS (phosphate-buffered saline) solution to a concentration of 1 to 10 µg/ml, onto the sensor; and
   reacting the dropped solution for 10 to 600 seconds.

10. The sensor of claim 1, wherein the hydrogel is synthesized by a photopolymerized reaction with a polymer monomer, a polymer cross-linker, and boronic acid in the porous membrane substrate, wherein the polymer monomer is N-(2-hydroxyethyl)acrylamide, the polymer cross-linker is N,N'-methylene-bisacrylamide, and the boronic acid is 3-(acrylamido) phenylboronic acid.

11. The sensor of claim 10, wherein concentration (w/v) of the polymer monomer and the boronic acid for the synthesis into the reactive layer is within a range of 4:1 to 100:1.

* * * * *